Dec. 20, 1955 G. MERRILL Plant Pat. 1,440
PEACH TREE
Filed Feb. 14, 1955
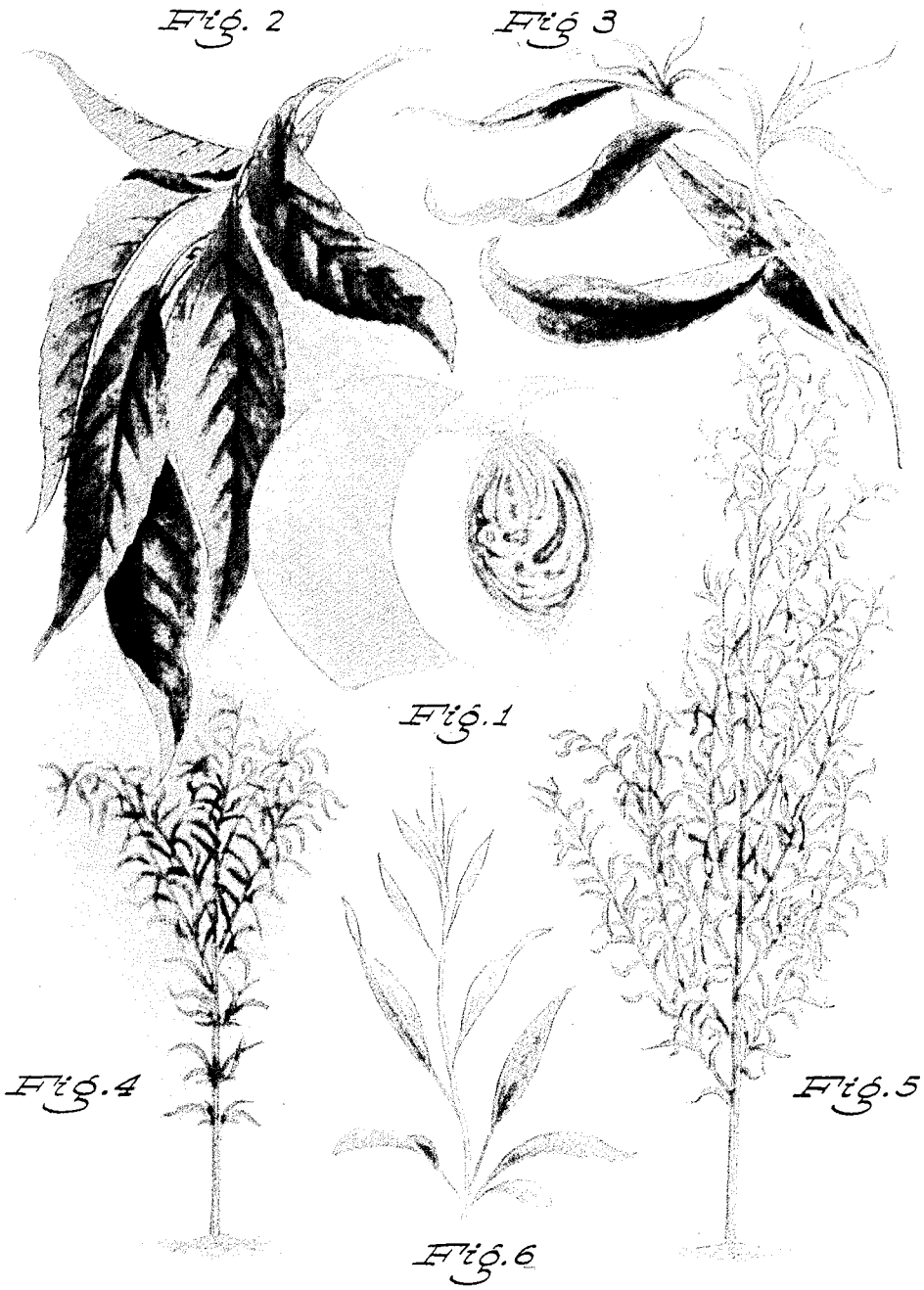
WITNESS
Addison E. Avery
INVENTOR
Grant Merrill
Webster & Webster
ATTYS.

United States Patent Office

Plant Pat. 1,440
Patented Dec. 20, 1955

1,440

PEACH TREE

Grant Merrill, Red Bluff, Calif.

Application February 14, 1955, Serial No. 488,179

1 Claim. (Cl. 47—62)

This discovery relates to a new and distinct variety of peach tree which bears fruit whose seeds are of especial value in the propagation of seedlings for use as root stock; such seedlings being particularly and advantageously characterized firstly by high resistance to nematode infestation, and secondly—in a great percentage of seedlings—by blood or red leaves.

The first mentioned novel characteristic is desirable in order to maintain strong, sturdy root stock during the life of the commercial fruit bearing variety which is budded or grafted onto the seedling; the second characteristic, as above, making possible faster and more accurate suckering—by reason of the readily visible blood or red leaves—of a seedling after the budding or grafting thereon of the commercial fruit bearing variety.

A further distinctive characteristic of the present variety of peach tree is that its seeds produce excellent nursery stock in that most of the resultant seedlings are straight, upright, and very uniform in growth. Such growth is advantageous—in root stock seedlings—as it facilitates easy and ready budding and other handling in the nursery.

A still further distinctive feature of the present variety of peach tree is that the seeds have an excellent germination ratio relative to failures; this being of economical advantage to the nurseryman who grows the seedlings for root stock use.

An additional feature of the present variety of peach tree is that it is a regular and productive bearer under normal agricultural care, and the fruit is freestone, which makes it possible to effect easy removal of the seeds for subsequent use in the propagation of root stock seedlings.

The instant variety of peach tree was discovered and subsequently asexually reproduced by me in the following manner:

During the course of recurrent inspection of the peach trees growing in my orchard near Bakersfield, Kern County, California, I observed the parent tree growing as a sucker, originating below ground, from the root stock of a Merrill Beauty Peach (United States Plant Patent No. 905); the root stock—as far as known—being believed to be that which is grown as the S-37 (United States Plant Patent No. 904).

I recognized that such sucker was growing quite vigorously, yet in an area where nematode infestation was very severe. I therefore undertook asexual reproduction from such parent tree by grafting onto other trees in the orchard near Bakersfield, California, and by June budding in my test orchard near Red Bluff, Tehama County, California. Seeds from the trees so grafted and budded were then planted in a badly nematode infested area of the orchard near Bakersfield, California, and the resultant seedlings were subsequently dug, whereupon it was determined—because of the small number of nematode galls on the roots—that such seedlings were very resistant to nematodes; such testing having also been made in comparison to certain other varieties, as will hereinafter appear.

Additionally, the testing of the variety evidenced the fact that in a high percentage of the seedlings the foliage was blood or red leaved.

Subsequent asexual reproductions of the parent tree run true in all respects, including the production of seeds which, when planted, produce seedlings distinctively characterized as described.

In the drawings:

Fig. 1 is an elevation of a pair of the fruit of the instant variety; one of such fruit being in sectional elevation with the stone exposed.

Fig. 2 is an elevation of a twig and leaves, in fall growth, of a mature tree.

Fig. 3 is an elevation of a twig and leaves, in spring growth, of a mature tree.

Fig. 4 is an elevation of one of the root stock seedlings, in spring growth, produced from a seed of the present variety.

Fig. 5 is an elevation of one of the root stock seedlings, in fall growth, produced from a seed of the present variety.

Fig. 6 is an enlarged fragmentary elevation showing a sucker twig and leaves, in enlargement, of one of said seedlings at the time of suckering.

Referring now more specifically to the pomological details of this new and distinct variety of peach tree, the following is an outline description thereof; all major color plate identifications being by reference to Maerz and Paul Dictionary of Color:

Tree: Medium size. Form and density controlled by pruning. Productive and regular bearer under normal orchard care.

Trunk: Medium stocky; medium shaggy.

Branches: Slender; fairly smooth; brownish red—becoming grey on the older limbs.

*Lenticels.*—Medium size; more numerous than normal in most peach trees.

Leaves.—Mature: Large size; average length—6 15/16"; average width—1 7/8". Lanceolate with acuminate tip, acutely pointed. Medium thickness. Smooth, except for a rugose condition along the midrib.

*Margin.*—Finely serrate

*Petiole.*—Medium length; medium size

*Glands.*—Two to three in number; alternate; very small; globose; about half attached to leaf and half to petiole; dark purple in color

*Stipules.*—Present on new growth; dropping off early.

Leaves.—Young: Variable in size but otherwise similar to mature leaves in shape and other characteristics.

Leaves.—Color:

Young or spring leaves of mature tree (see Fig. 3)—red (6-L-1) in a majority of the leaves; a few being green (21-L-6); the older of the red leaves having an olive cast (15-L-10) on the upper side, and the under side shading to a darker or brownish red (7-J-7).

Fall leaves of mature tree (see Fig. 2).

Top side—medium green (22-L-7).

Under side—lighter green (22-K-3); certain of the leaves showing a reddish tinge on the under side, and the larger veins on such under side being red.

The seedlings, grown from the seeds of the present variety, as shown in Figs. 4 and 5, and the suckering growth thereof as shown in Fig. 6, are predominately characterized by the blood or reddish color of the leaves.

Generally there occurs transitions, on a tree, in various stages between the very red leaves of the new growth and the older leaves as they appear in the fall.

Flower buds: Medium large; medium length; plump; free; pubescent.

Flowers: Dates of first and full bloom—on or about March 3, 1954, and March 18, 1954, respectively, at Red Bluff, California.
Midseason.
Large.
Many petaled and double.
Medium pink color.

Fruit: Dates of first and last picking—firm ripe on or about August 25, 1954; full ripe strip picking, for securing seeds, on or about August 31, 1954, at Red Bluff, California.
*Size.*—Uniform; small; average diameter—2 5/16" average length—2 3/8".
*Form.*—Uniform; fairly symmetrical; almost globose.
*Suture.*—Distinct; shallow; extends from base to slightly beyond; slight depression beyond the pistil point.
*Ventral surface.*—Slightly lipped toward base on both sides; lips unequal.
*Cavity.*—Elongated in suture plane with suture showing on one side and slightly across the other; average depth—3/8"; average breath—3/4"; flaring; markings—none.
*Base.*—Rounded.
*Apex.*—Short, rounded to truncate.
*Pistil point.*—Apical.

Skin: Thick; tough; slightly astringent. Frees readily from the flesh. No tendency to crack.
*Down.*—Moderate; short; rolls up when rubbed
*Color.*—Light greenish yellow near base (11–K–4, shading to 11–G–5), becoming darker (13–K–6) in the direction of the apex, with a dull pink blush (11–A–7).

Flesh:
*Fibers.*—Abundant; pink; tough.
*Amygdalin.*—Wanting.
*Juice.*—Moderate.
*Texture.*—Medium coarse.
*Ripens.*—Evenly.
*Flavor.*—Flat.
*Aroma.*—Wanting.
*Eating quality.*—Inferior.
*Color.*—Pale cream or yellow (11–H–1), shading slightly darker yellow (10–F–3), with the surface of the pit cavity pinkish red or rose (3–H–3, shading to 3–J–4).

Stone: Free; parts from flesh smoothly. Medium size.
*Average length.*—1 7/16"; average breadth 1"; average thickness—1 3/16".
*Form.*—Obovate.
*Base.*—Straight.
*Hilum.*—Oval.
*Apex.*—Acuminate.
*Sides.*—Unequal, curved on right and left.
*Surface.*—Regularly furrowed throughout; ridged near base; pitted from base to above center.
*Ridges.*—Rounded; interrupted.
*Pits.*—Elongated.
*Ventral edge.*—Thick.
*Dorsal edge.*—Narrow, shallow with narrow groove throughout.
*Color.*—Brown (8–L–6).

The above described new and distinct variety of peach tree is of commercial use solely for the production of its seeds, from which root stock seedlings are grown; such seedlings—as hereinbefore recited—being highly resistant to nematode infestation, and in a great percentage of cases having foliage which is predominately blood or red leaved.

Seedlings produced from seeds of the present variety have resistance to nematode infestation at least as high as the S–37 (United States Plant Patent No. 904) root stock peach variety, but which seedlings are advantageously distinct by reason not only of the blood or red leaves, but also the straight, upright, and uniform growing habit of most of such seedlings. The blood or red leaves of the seedlings contribute substantially to the ease of suckering, for the reason that the parts to be removed from the root stock, after the commercial fruit variety is budded thereon, can be readily visually observed and distinguished.

Further, the straight, upright, and uniform growing habit of the seedlings permits of easier budding, and more convenient handling by the nurseryman.

Seedlings of the present variety have been grown by me in extensive comparative tests, and under like growing conditions, with a number of other varieties, such as:

From the University of California, at Davis, California:
Shalil 142–15; 63852–15–23; 36485–21–22–23; 55855; 55886; 63850–19:23.
Yunnan 55888; 55887.
Bokhara.

From the United States Department of Agriculture Plant Introduction Gardens at Chico, California:
PI 141204–D3836; PI 135994–E 6–32; PI 141204–D3837; PI 135994–E–6–32; PI 141202–D40–30; PI 135994–E8–41; PI 135994–E8–38; PI 141202–D40–29.

From other sources:
Stribling S–37.
Carolina Naturals.
Tennessee Red Leaf.

As a result of such tests, seedlings of the present variety are at least as resistant to nematode infestation as the most resistant of any of the others, as above, and in addition shows better habits of growth, coupled with the red or blood leaf characteristic. The seedlings of no other red or blood leafed variety approached the seedlings of the present variety in its resistance to nematode infestation.

Having thus described the invention I claim:

A new and distinct variety of peach tree, as illustrated and described, characterized by regular and productive bearing of freestone fruit whose seeds have an excellent ratio of germination relative to failures, and which seeds produce seedlings—for root stock—which are highly resistant to nematode infestation, and a great percentage of said seedlings being blood or red leaved; the variety being further characterized by a high ratio of germination of the seeds, and a straight, upright, and uniform habit of growth of most of the resultant seedlings.

No references cited.